United States Patent
Seward et al.

(10) Patent No.: US 6,171,247 B1
(45) Date of Patent: Jan. 9, 2001

(54) UNDERFLUID CATHETER SYSTEM AND METHOD HAVING A ROTATABLE MULTIPLANE TRANSDUCER

(75) Inventors: James Bernard Seward; Abdul Jamil Tajik, both of Rochester, MN (US)

(73) Assignee: Mayo Foundation for Medical Education and Research, Rochester, MN (US)

( * ) Notice: Under 35 U.S.C. 154(b), the term of this patent shall be extended for 0 days.

(21) Appl. No.: 08/874,792

(22) Filed: Jun. 13, 1997

(51) Int. Cl.[7] .................................................. A61B 8/12
(52) U.S. Cl. ..................... 600/459; 600/466; 600/467; 128/916
(58) Field of Search ................................ 600/439, 459, 600/462, 466, 447, 467; 128/916

(56) References Cited

U.S. PATENT DOCUMENTS

| | | |
|---|---|---|
| 3,789,833 | 2/1974 | Bom . |
| 3,938,502 | 2/1976 | Bom . |
| 4,028,934 | 6/1977 | Sollish . |

(List continued on next page.)

FOREIGN PATENT DOCUMENTS

| | | |
|---|---|---|
| 44 23 808 A1 | 1/1995 | (DE) . |
| 0 234 951 | 9/1987 | (EP) . |
| 0 284 055 A2 | 9/1988 | (EP) . |
| 0 600 568 | 6/1994 | (EP) . |
| 0 642 762 A2 | 3/1995 | (EP) . |
| WO 90/13260 | 11/1990 | (WO) . |
| WO 91/04707 | 4/1991 | (WO) . |
| WO 93/08738 | 5/1993 | (WO) . |
| WO 94/16625 | 8/1994 | (WO) . |
| WO 95/13111 | 5/1995 | (WO) . |
| WO 95/19143 | 7/1995 | (WO) . |
| WO 96/00522 | 1/1996 | (WO) . |
| WO 96/03918 | 2/1996 | (WO) . |
| WO 96/03921 | 2/1996 | (WO) . |
| WO 96/03922 | 2/1996 | (WO) . |
| WO 96/04588 | 2/1996 | (WO) . |

OTHER PUBLICATIONS

Weintraub et al., "Realtime Intracardiac Two–Dimensional Echocardiography in the Catheterization Laboratory in Humans". Abstract *JACC* vol. 15, No. 2, 16A (Feb. 1990).

Pandian et al., "Intracardiac Echocardiography. Experimental Observations on Intracavitary Imaging of Cardiac Structures with 20–MHz Ultrasound Catheters", *Echocardiography*, vol. 8, No. 1 (Jan. 1991) pp. 127–134.

"Cardiovascular Imaging Systems' Intracardiac Imaging Catheter", *M–D–D–I Reports*, publisher: F–D–C Reports, Inc., pp I&W–6 and I&W–7 (Mar. 30, 1992).

Moriuchi et al., "Transvenous Echocardiography: Experimental Feasibility Study", *Jpn J Med Ultrasonics*, vol. 19, No. 3 (1992), pp. 228–235.

Nishimura et al., "Intravascular Ultrasound Imaging: In Vitro Validation and Pathologic Correlation", *JACC*, vol. 16, No. 1 (Jul. 1990) pp. 145–154.

(List continued on next page.)

*Primary Examiner*—Marvin M. Lateef
*Assistant Examiner*—Shawna J Shaw
(74) *Attorney, Agent, or Firm*—Merchant & Gould P.C.

(57) ABSTRACT

A self-contained ultrasound catheter device capable of delivering diagnostic and therapeutic tools in a field of ultrasound includes a rotatable multiplane sector phased array imaging ultrasound transducer used for the visualization of under fluid structures and/or diagnostic and therapeutic events. The multiplane sector phased array is rotatable around an axis of an ultrasound beam to obtain sequential imaging planes in a continuous or interrupted sweep up to 360 degrees. The transducer being a multiplane transducer allows more versatile visualization of underfluid structures and/or events. The sequential acquisition of tomographic images is suitable for 3-dimensional image reconstruction.

25 Claims, 7 Drawing Sheets

U.S. PATENT DOCUMENTS

| | | | |
|---|---|---|---|
| 4,110,723 | 8/1978 | Hetz et al. . | |
| 4,354,502 * | 10/1982 | Colley et al. . | |
| 4,374,525 | 2/1983 | Baba . | |
| 4,391,282 | 7/1983 | Ando et al. . | |
| 4,462,408 | 7/1984 | Silverstein et al. . | |
| 4,466,444 | 8/1984 | Baba . | |
| 4,543,960 | 10/1985 | Harul et al. . | |
| 4,550,607 | 11/1985 | Maslak et al. | 73/626 |
| 4,582,067 | 4/1986 | Silverstein et al. | 128/663 |
| 4,699,009 | 10/1987 | Maslak et al. | 73/626 |
| 4,748,985 | 6/1988 | Nagasaki . | |
| 4,757,821 * | 7/1988 | Snyder . | |
| 4,771,788 | 9/1988 | Millar | 128/661.09 |
| 4,794,931 | 1/1989 | Yock | 128/660.03 |
| 4,802,487 | 2/1989 | Martin et al. . | |
| 4,841,977 | 6/1989 | Griffith et al. | 128/344 |
| 4,841,979 | 6/1989 | Dow et al. . | |
| 4,869,256 | 9/1989 | Kanno et al. . | |
| 4,869,258 | 9/1989 | Hetz . | |
| 4,887,605 | 12/1989 | Angelsen et al. | 128/660.03 |
| 4,911,170 | 3/1990 | Thomas, III et al. | 128/662.06 |
| 4,917,097 | 4/1990 | Proudian et al. | 128/662.06 |
| 4,930,515 | 6/1990 | Terwilliger . | |
| 4,936,281 | 6/1990 | Stasz | 128/660.03 |
| 4,947,852 | 8/1990 | Nassi et al. | 128/662.06 |
| 4,951,677 | 8/1990 | Crowley et al. | 128/662.06 |
| 4,957,111 | 9/1990 | Millar | 128/662.06 |
| 5,000,185 | 3/1991 | Yock . | |
| 5,002,059 | 3/1991 | Crowley et al. | 128/662.06 |
| 5,010,886 | 4/1991 | Passafaro et al. . | |
| 5,014,710 | 5/1991 | Maslak et al. | 128/660.05 |
| 5,022,399 | 6/1991 | Biegeleisen | 128/662.06 |
| 5,029,588 | 7/1991 | Yock et al. | 128/662.06 |
| 5,038,789 | 8/1991 | Frazin | 128/662.06 |
| 5,070,879 | 12/1991 | Herres . | |
| 5,076,278 | 12/1991 | Vilkomerson et al. | 128/662.03 |
| 5,076,279 | 12/1991 | Arenson et al. | 128/662.05 |
| 5,081,993 * | 1/1992 | Kitney et al. . | |
| 5,105,819 | 4/1992 | Wollschläger et al. | 128/662.06 |
| 5,107,844 | 4/1992 | Kami et al. . | |
| 5,115,814 * | 5/1992 | Griffith et al. . | |
| 5,125,410 | 6/1992 | Misono et al. . | |
| 5,135,001 | 8/1992 | Sinofsky et al. . | |
| 5,140,558 | 8/1992 | Harrison, Jr. et al. | 367/7 |
| 5,148,810 | 9/1992 | Maslak et al. | 128/661.01 |
| 5,152,294 | 10/1992 | Mochizuki et al. . | |
| 5,159,931 | 11/1992 | Pini . | |
| 5,161,537 | 11/1992 | Hashimoto et al. | 128/662.06 |
| 5,165,413 | 11/1992 | Maslak et al. | 128/660.05 |
| 5,174,296 | 12/1992 | Watanabe et al. . | |
| 5,181,514 | 1/1993 | Solomon et al. . | |
| 5,183,048 | 2/1993 | Eberle . | |
| 5,186,175 | 2/1993 | Hirama et al. . | |
| 5,186,177 | 2/1993 | O'Donnell et al. | 128/662.06 |
| 5,193,546 | 3/1993 | Shaknovich | 128/662.06 |
| 5,199,433 * | 4/1993 | Metzger et al. . | |
| 5,199,437 | 4/1993 | Langberg . | |
| 5,211,168 | 5/1993 | Mason et al. . | |
| 5,215,092 | 6/1993 | Wray . | |
| 5,222,501 | 6/1993 | Ideker et al. | 128/660.03 |
| 5,226,422 | 7/1993 | McKeighen et al. . | |
| 5,235,986 | 8/1993 | Maslak et al. | 128/661.01 |
| 5,243,988 | 9/1993 | Sieben et al. . | |
| 5,257,629 | 11/1993 | Kitney et al. . | |
| 5,261,408 | 11/1993 | Maslak et al. | 128/661.01 |
| 5,285,788 | 2/1994 | Arenson et al. | 128/660.05 |
| 5,291,893 | 3/1994 | Slayton | 128/662.06 |
| 5,295,486 | 3/1994 | Wollschläger et al. . | |
| 5,297,553 | 3/1994 | Sliwa, Jr. et al. | 128/662.03 |
| 5,299,578 | 4/1994 | Rotteveel et al. . | |
| 5,305,755 | 4/1994 | Nakao . | |
| 5,305,756 | 4/1994 | Entrekin et al. | 128/660.09 |
| 5,311,871 | 5/1994 | Yock | 128/662.95 |
| 5,313,949 | 5/1994 | Yock . | |
| 5,320,104 | 6/1994 | Fearnside et al. . | |
| 5,325,860 | 7/1994 | Seward et al. . | |
| 5,329,496 | 7/1994 | Smith | 367/140 |
| 5,329,927 | 7/1994 | Gardineer et al. . | |
| 5,343,865 | 9/1994 | Gardineer et al. . | |
| 5,345,940 | 9/1994 | Seward et al. . | |
| 5,351,691 | 10/1994 | Brommersma . | |
| 5,360,007 | 11/1994 | Shinomura et al. . | |
| 5,373,845 | 12/1994 | Gardineer et al. | 128/660.09 |
| 5,373,849 | 12/1994 | Maroney et al. . | |
| 5,377,685 | 1/1995 | Kazi et al. . | |
| 5,385,148 | 1/1995 | Lesh et al. | 128/662.06 |
| 5,398,689 * | 3/1995 | Connor et al. . | |
| 5,402,793 | 4/1995 | Gruner et al. . | |
| 5,415,175 | 5/1995 | Hanafy et al. | 128/662.03 |
| 5,421,336 | 6/1995 | De Bernardis . | |
| 5,425,370 | 6/1995 | Vilkomerson . | |
| 5,437,283 | 8/1995 | Ranalletta et al. | 600/463 |
| 5,438,997 | 8/1995 | Sieben et al. . | |
| 5,438,998 | 8/1995 | Hanafy | 128/662.03 |
| 5,460,181 | 10/1995 | Seyed-Bolorforosh . | |
| 5,464,016 | 11/1995 | Nicholas et al. . | |
| 5,465,724 | 11/1995 | Sliwa, Jr. et al. . | |
| 5,467,779 | 11/1995 | Smith et al. . | |
| 5,469,852 | 11/1995 | Nakamura et al. . | |
| 5,474,075 | 12/1995 | Goldberg et al. . | |
| 5,479,929 * | 1/1996 | Cooper et al. . | |
| 5,479,930 | 1/1996 | Gruner et al. . | |
| 5,485,846 * | 1/1996 | Webler et al. . | |
| 5,487,388 | 1/1996 | Rello et al. . | |
| 5,499,630 | 3/1996 | Hiki et al. . | |
| 5,503,152 | 4/1996 | Oakley et al. . | |
| 5,549,111 | 8/1996 | Wright et al. | 128/742 |
| 5,569,276 * | 10/1996 | Jang et al. . | |
| 5,630,416 | 5/1997 | Uchikura et al. . | |
| 5,634,464 * | 6/1997 | Jang et al. . | |
| 5,697,377 | 12/1997 | Wittkampf . | |
| 5,699,805 * | 12/1997 | Seward et al. . | |
| 5,704,361 | 1/1998 | Seward et al. . | |
| 5,713,363 | 2/1998 | Seward et al. . | |
| 5,749,833 * | 5/1998 | Hakki et al. . | |
| 5,876,345 * | 3/1999 | Eaton et al. | 600/466 |
| 5,904,651 * | 3/1999 | Swanson et al. | 600/407 |

OTHER PUBLICATIONS

Pandian et al., "Intracardiac, Intravascular, Two–Dimensional, High–Frequency Ultrasound Imaging of Pulmonary Artery and Its Branches in Humans and Animals", *Circulation*, vol. 81, No. 6 (Jun. 1990) pp. 2007–2012.

Bom et al., "Early and Recent Intraluminal Ultrasound Devices", *International Journal of Cardiac Imaging*, vol. 4 (1989) pp. 79–88.

Schwartz et al., "Intracardiac Echocardiographic Guidance and Monitoring During Aortic and Mitral Balloon Valvuloplasty: In Vivo Experimental Studies", Abstract, *JACC*, vol. 15, No. 2, 104A (Feb. 1990).

Hung et al., "Usefulness of Intracardiac Echocardiography in Transseptal Puncture During Percutaneous Transvenous Mitral Commissurotomy", Section of Cardiology, Chang Gung Med. Col. and Chang Gung Memorial Hospital, (May 10, 1993) p. 853.

Weintraub et al., "Intracardiac Two–dimensional Echocardiography in Patients with Pericardial Effusion and Cardiac Tamponade", *Journal Am Soc. of Echocardiography*, vol. 4, No. 6, (Nov.–Dec. 1991) pp. 571–576.

Schwartz et al., Intracardiac Echocardiographic Imaging of Cardiac Abnormalities, Ischemic.

Myocardial Dysfunction, and Myocardial Perfusion: Studies With a 10 MHz Ultrasound Catheter, *Journal Am Soc. of Echocardiography*, vol. 6, No. 4, (Jul.–Aug. 1993) pp. 345–355.

Rothman et al., "Intraluminal Ultrasound Imaging Through a Balloon Dilation Catheter in an Animal Model of Coarctation of the Aorta", *Circulation*, vol. 85, No. 6 (Jun. 1992) pp. 2291–2295.

Schwartz et al., "Intracardiac echocardiography without fluoroscopy: Potential of a balloon–tipped, flow–directed ultrasound catheter", *Am. Heart Journal*, vol. 129, No. 3 (Mar. 1995) pp. 598–603.

Kremkau, Frederick, "AAPM Tutorial. Multiple–Element Transducers", *RadioGraphics*, (Sep. 1993) pp. 1163–1176.

Bom et al., "Intravascular Ultrasound: Newest Branch of the Echo–Tree", *Cardiovascular Imaging*, vol. 4 (1992) pp. 55–59.

Seward, et al., "Ultrasound Cardioscopy: Embarking on a New Journey", *Mayo Clin Proc.*, vol. 71, No. 7, (Jul. 1996), pp. 629–635.

Kossoff, et al., "Real–time quasi–three–dimensional viewing in sonography, with conventional, gray–scale volume imaging", *Ultrasound Obstet. Gynecol.*, vol. 4, (1994), pp. 211–216.

Entrekin, et al., "Real–time 3–D ultrasound imaging with a 1–D 'fan beam' transducer array", *SPIE*, vol. 1733 (1992), pp. 264–272.

Smith et al., "High–Speed Ultrasound Volumetric Imaging System—Part I: Transducer Design and Beam Steering", *IEEE Transactions on Ultrasonics, Ferroelectrics, and Frequency Control*, vol. 38, No. 2 (Mar. 1991), pp. 100–108.

von Ramm, et al., "High Speed Ultrasound Volumetric Imaging System—Part II: Parallel Processing and Image Display", *IEEE Transactions on Ultrasonics, Ferroelectrics, and Frequency Control*, vol. 38, No. 2 (Mar. 1991), pp. 109–115.

Devonald, et al., "Volume Imaging: Three–Dimensional Appreciation of the Fetal Head and Face", *J. Ultrasound Med.*, vol. 14 (1995), pp. 919–925.

Talbert, D.G., "An 'Add–On' Modification for Linear Array Real Time Ultrasound Scanners to Produce 3 Dimensional Displays". Conference: Ultrasonics International 1977. Brighton, England (Jun. 28–30, 1997), copy 128/916, pp. 52–67.

Seward et al., "Transvascular and Intracardiac Two–Dimensional Echocardiography", *Echocardiography*, vol. 7, No. 4 (Jul. 1990) pp. 457–464.

Schwartz et al., "Real–Time Intracardiac Two–Dimensional Echocardiography: An Experimental Study of In Vivo Feasibility, Imaging Planes, and Echocardiographic Anatomy", *Echocardiography*, vol. 7, No. 4 (1990) pp. 443–455.

Schwartz et al., "Intracardiac Echocardiography in Humans Using a Small–Sized (6F), Low Frequency (12.5MHz) Ultrasound Catheter", *JACC*, vol. 21, No. 1 (Jan. 1993) pp. 189–198.

Pandian et al., "Real–Time, Intracardiac, Two–Dimensional Echocardiography. Enhanced Depth of Field with a Low––Frequency (12.5MHz) Ultrasound Catheter", *Echocardiography*, vol. 8, No. 4 (1991) pp. 407–422.

Tardif et al., "Intracardiac Echocardiography With a Steerable Low–Frequency Linear–Array Probe for Left–Sided Heart Imaging From the Right Side: Experimental Studies", *Journal Am. Soc. of Echocardiography*, vol. 8, No. 2 (Mar.–Apr. 1995) pp. 132–138.

Schwartz et al., "Intracardiac echocardiography during simulated aortic and mitral balloon valvuloplasty: In vivo experimental studies", *Am. Heart Journal*, vol. 123, No. 3 (Mar. 1992) pp. 665–674.

Seward et al., "Multiplane Transesophageal Echocardiography: Image Orientation, Examination Technique, Anatomic Correlations and Clinical Applications", *Mayo Clinic Proceedings*, (1993) 68:523–551.

McCann et al., "Multidimensional Ultrasonic Imaging for Cardiology", *Proc IEEE*, (1988) 76: 1063–1071.

Belohlavek et al., "Three–and Four–Dimensional Cardiovascular Ultrasound Imaging: A New Era for Echocardiography", *Mayo Clinic Proceedings*, (1993)68:221–240.

* cited by examiner

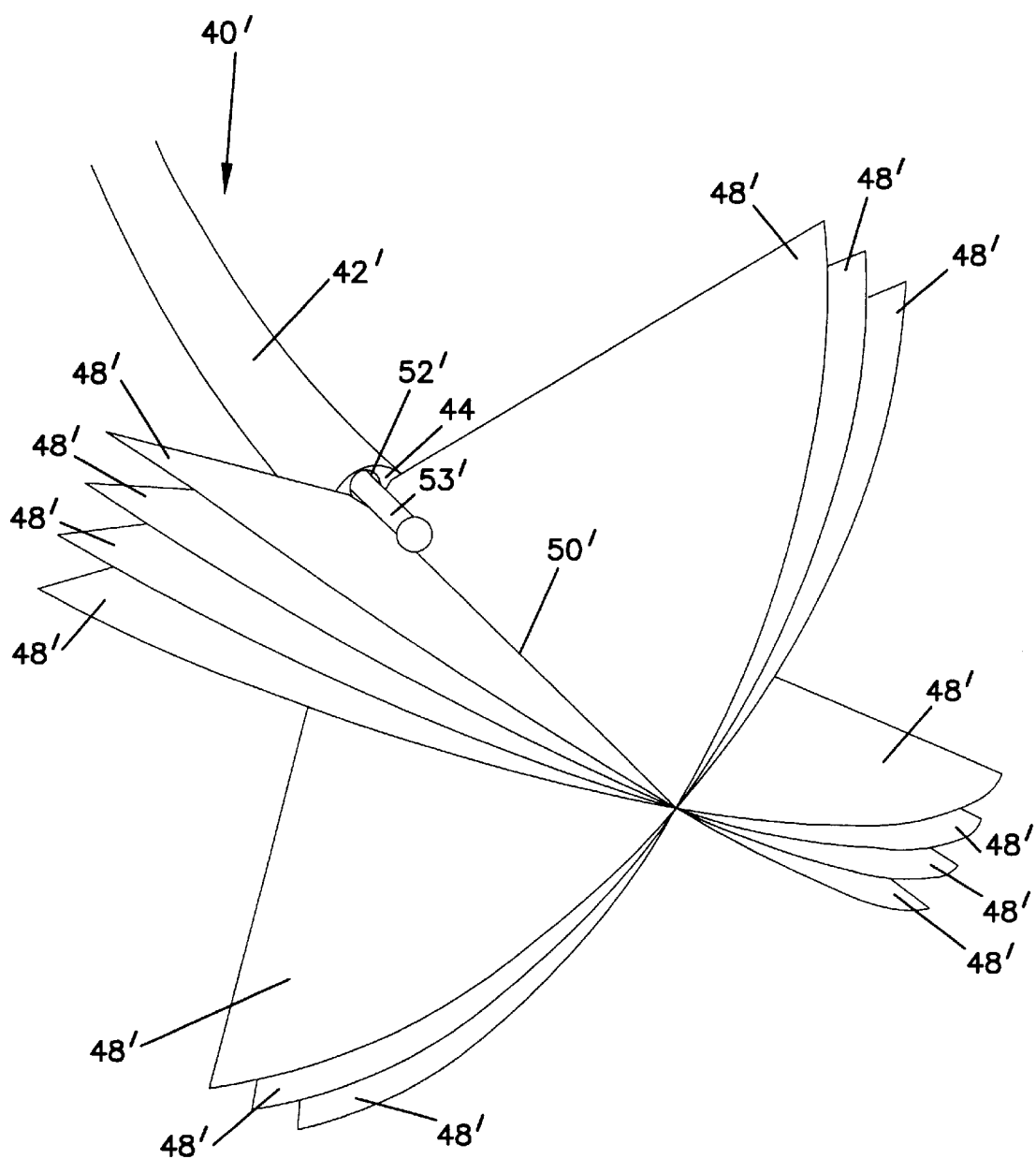

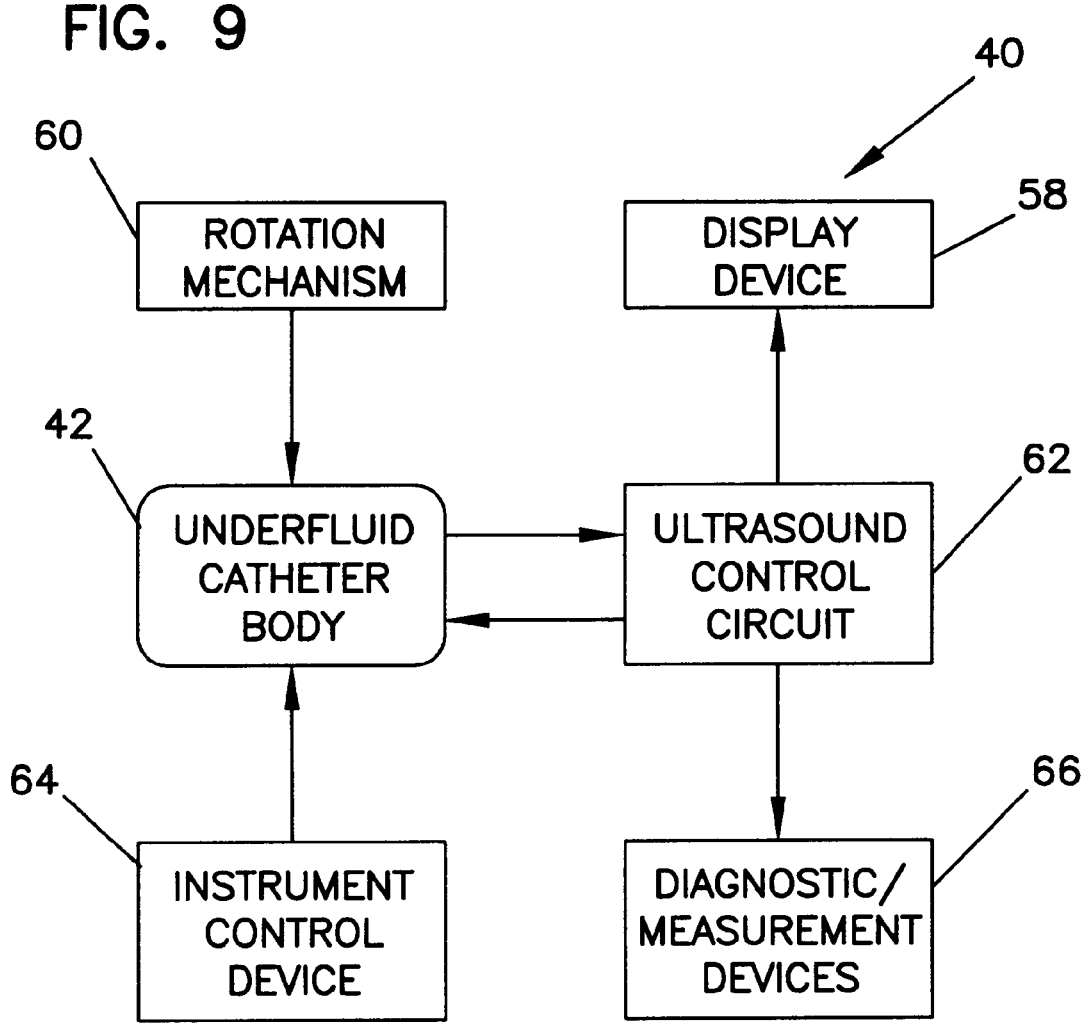

ated multiple fields of view while requiring no manipulation of the catheter. There is also a need for a catheter-based imaging device capable of providing spatially sequenced tomographic images that can be formed, i.e. coalesced, into a three-dimensional image by using a catheter-based multiplane array technology. There is further a need for a catheter-based imaging device capable of delivering diagnostic and
UNDERFLUID CATHETER SYSTEM AND METHOD HAVING A ROTATABLE MULTIPLANE TRANSDUCER

FIELD OF THE INVENTION

The present invention relates generally to a catheter-based ultrasound imaging device having a rotatable multiplane transducer which can obtain spatially related sets of 2-dimensional images that can be reformatted into a 3-dimensional volumetric image.

BACKGROUND OF THE INVENTION

In the catheter-based ultrasound imaging arena, increasing emphasis is being placed on intraluminal/intracavitary underfluid imaging for the purpose of directing precision therapy and diagnostics. A number of imaging catheter inventions have been proposed over the last few years. The basic concepts of a self-contained ultrasound catheter device have been described in the patents issued to Dr. James B. Seward and A. Jamil Tajik, such as U.S. Pat. Nos. 5,325,860 and 5,345,940, and are incorporated hereby by references. However, at present, underfluid ultrasound technology is principally limited to linear, sector, or cylindrical ultrasound array transducers which are optimized to obtain single tomographic planes of view. Additional planes are usually obtained by manipulation of the catheter or the stacking of images into a data set. Three-dimensional volumetric images have been small and of little clinical utility.

Presently rotatable multiplane arrays are primarily used in large transesophageal echocardiographic probes (see "Multiplane Transesophageal Echocardiography: Image Orientation, Examination Technique, Anatomic Correlations and Clinical Applications" by Seward J. B., et al. Mayo Clinic Proceedings, 68:523–551, 1993) and, to a lesser extent, for surface echocardiographic examinations (see "Multidimensional Ultrasonic Imaging for Cardiology" by McCann H. A. et al. Proc IEEE, 76:1063–1071, 1988; and U.S. Pat. No. 4,543,960 issued to Harui et al.) The patent discloses a catheter-based multiplane (conical data set) echocardiography scanhead. The ultrasound imaging scanhead is rotated to obtain multiple cross-sectional planes from within the cardiovascular system including the heart. This patent also discloses that it is possible to use the scanhead in a manner whereby cross-sectional views of the heart can be obtained along a variety of orientations. These catheter orientations are selectable by the operator while actually viewing the internal cardiovascular and surrounding structures on the monitor to which the scanhead is connected. The catheter-based multiplane echocardiographic technology permits the attainment of sequential tomographic images (i.e., a data set) from the confines of the cardiovascular system. Such multiplane transducers have been used to obtain a spatially sequenced set of images suitable for 3-dimensional image reconstruction (see "Three- and Four-Dimensional Cardiovascular Ultrasound Imaging: A New Era for Echocardiography" by Belohlavek M. et al. Mayo Clinic Proceedings 1993, 68:221–240).

There is a need in the art for a catheter-based intraluminal/intracavital transluminal imaging device capable of generating multiple fields of view while requiring no manipulation of the catheter. There is also a need for a catheter-based imaging device capable of providing spatially sequenced tomographic images that can be formed, i.e. coalesced, into a three-dimensional image by using a catheter-based multiplane array technology. There is further a need for a catheter-based imaging device capable of delivering diagnostic and therapeutic tools into a field of ultrasound generated by a multiplane phased array imaging ultrasound transducer.

SUMMARY OF THE INVENTION

The present invention relates generally to a volumetric, 3-dimensional imaging underfluid catheter system, particularly, to a catheter-based ultrasound imaging device having a rotatable multiplane transducer for the acquisition of sequential tomographic images in a variable arc up to 360 degrees.

The present invention further relates to a self-contained ultrasound catheter device capable of delivering diagnostic and therapeutic tools into a field of ultrasound generated by the rotatable phased array (or sector phased array) imaging ultrasound transducer.

In one embodiment of the present invention, an underfluid diagnostic and/or therapeutic catheter apparatus includes a catheter having proximal and distal ends and a multiplane ultrasound transducer array which is rotatably mounted proximate the distal end of the catheter for rotation about an axis. The multiplane ultrasound transducer array generates a plurality of sequential tomographic image planes which form a 3-dimensional image of an adjacent underfluid structure. The axis of rotation generally lies in the tomographic image planes.

Further in one embodiment, a working port is disposed in the catheter and extends from proximate the proximal end of the catheter to proximate the distal end of the catheter. The working port receives and delivers a medical instrument or other types of a working tool to proximate the distal end of the catheter. In other embodiments, multiple working ports can be disposed in the catheter for receiving and delivering medical instruments or other working tools. The medical instrument(s) or working tool(s) can be diagnostic or therapeutic devices. Exemplary medical instruments include catheters, angiographic catheters, ablation catheters, cutting tools, blades and balloons. Working ports can also be used to deliver medical drugs to localized regions. It is preferred for a working port to have an exit opening adjacent to the field of view of the transducer array so that the operation of the medical instrument(s) or other working tool(s) and the reaction therefrom can be observed in a real-time fashion. In alternative embodiments, no working port is disposed in the catheter. Medical instrument(s) or other working tool(s) at the distal end of the catheter adjacent to the field of view of the transducer array are mounted in such a way that the operation of the medical instrument(s) or other working tool(s) and the reaction therefrom can be observed in a real-time fashion.

Still in one embodiment, the multiplane ultrasound transducer array is a sector phased array. The sector phased array is mechanically or electronically or through other means rotated around an axis of the ultrasound beam which transmits and records the sector images in the sequential imaging planes in a continuous or interrupted sweep up to 360°. The field of view thus formed is a conical-type shaped volumetric field of view.

In one embodiment, the multiplane ultrasound transducer array is mounted facing transversely of a longitudinal axis of the catheter. The axis of rotation is generally perpendicular to the longitudinal axis of the catheter.

In another embodiment, the multiplane ultrasound transducer array is mounted facing along the longitudinal axis of the catheter. The axis of rotation extends generally along the longitudinal axis of the catheter.

Yet in one embodiment, the axis of rotating is offset from the longitudinal axis of the catheter.

The present invention also relates to a method of diagnosing and/or imaging an underfluid structure, comprising the steps of:
 providing a catheter apparatus comprising:
  a catheter, having a proximal end and distal end, including a body having a longitudinal axis;
  a multiplane ultrasound transducer array being rotatably mounted proximate the distal end of the catheter for rotation about an axis;
  the multiplane ultrasound transducer array generating a plurality of sequential tomographic image planes which form a 3-dimensional image of an underfluid structure, the axis of rotating lying in the tomographic image planes; and
  a working port disposed in the catheter and extending from proximate the proximal end to proximate the distal end of the catheter for receiving a medical instrument, the medical instrument being operable within a field of view of the 3-dimensional image;
 positioning the catheter proximate the underfluid structure;
 generating the sequential tomographic images which form the 3-dimensional image of the underfluid structure; and
 extending the medical instrument out of the working port and operating on the underfluid structure within a field of view of the 3-dimensional image.

Accordingly, one advantage of the present invention is that the catheter apparatus of the present invention is capable of generating wide fields of view while requiring no rotational manipulation of the catheter.

Another advantage is that the present catheter apparatus is a catheter-based imaging device capable of providing spatially sequenced tomographic images that can be formed, i.e. coalesced, into a three-dimensional image by using multiplane array technology.

Further another advantage is that the present catheter apparatus is also a catheter-based imaging device capable of delivering diagnostic and therapeutic tools into a field of ultrasound generated by a multiplane phased array imaging ultrasound transducer.

It is also noted that the underfluid (in particular underblood) utilization of ultrasound for diagnosis and direction of therapy is a recent development. Small sector phased arrays transducers are preferred for intracardiac and transvascular imaging because they characteristically have deeper penetration and better ergonomics compared to cylindrical or linear intraluminal transducers. Diagnostic and therapeutic tools can be manipulated into the ultrasound field for the purpose of ultrasonic visualization of various procedures, including underblood surgery and diagnostics. A principal limitation of a fixed phased array is that tools introduced into the ultrasound field of view frequently cannot be consistently kept within the plane of the tomographic image. A rotatable multiplane array in accordance with the principles of the present invention enhances the ability continuously visualize a tool within the tomographic field of view. Normally significant manipulation of the ultrasound catheter is necessary to view a procedure or tool and this is not always feasible, practical or safe. A rotatable multiplane array in the present invention greatly enhances maneuverability and visual versatility from the confines of a blood or fluid filled vessel, cavity or chamber.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

The accompanying drawings, which are incorporated in and constitute part of this specification, illustrate several embodiments of the present invention and together with the description, serve to explain the principles of the invention. A brief description of the drawings is as follows:

FIG. 8 is a partial schematic view of a catheter system having a medical instrument disposed in the field of view generated by an end-mounted multiplane transducer; and FIG. 9 is a block diagram of the catheter system.

DETAILED DESCRIPTION OF THE PREFERRED EMBODIMENT

Figure 1:
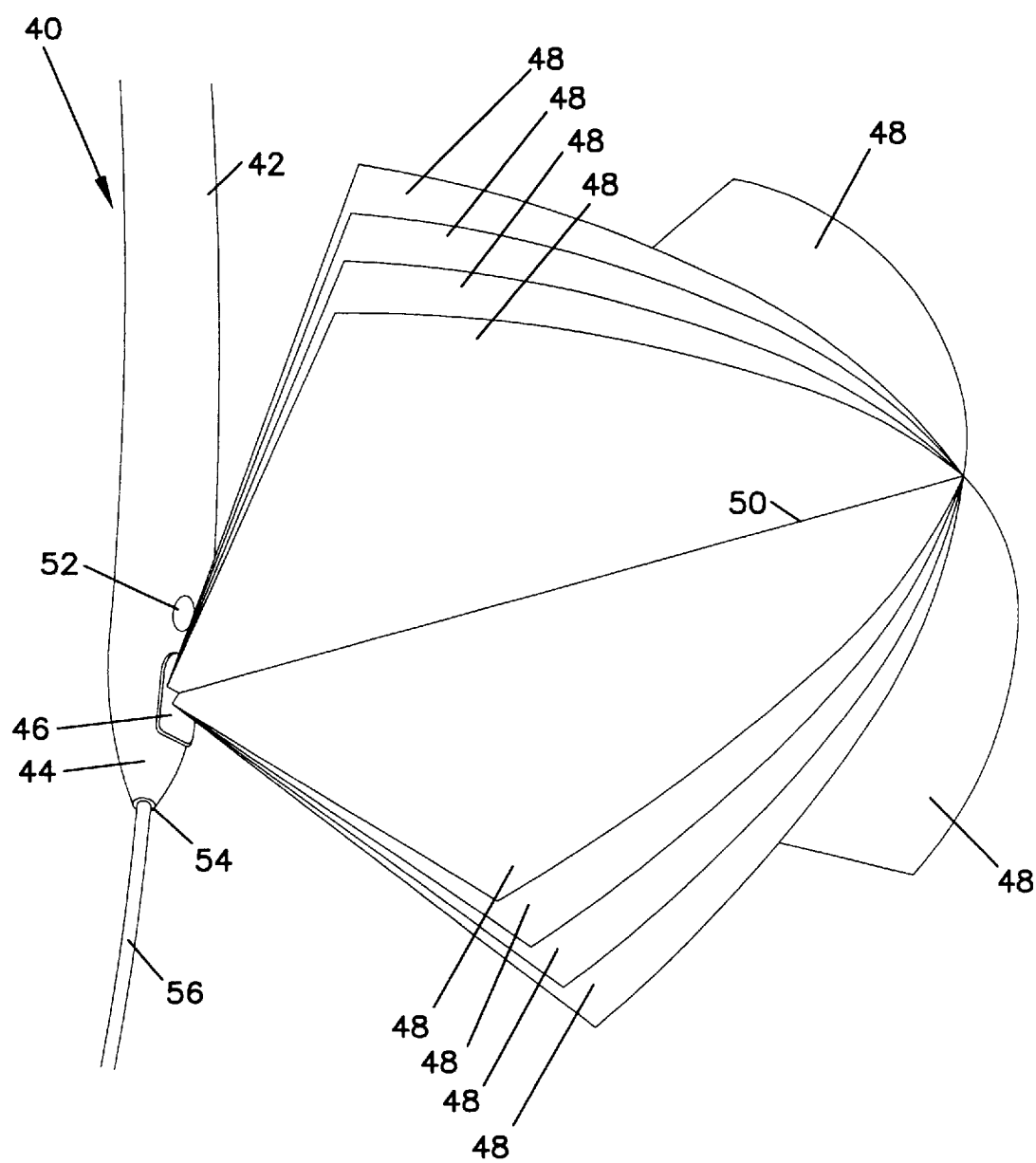
FIG. 1 is a partial schematic view of a first embodiment of a catheter system having a side-mounted multiplane transducer generating sequential imaging planes at a side of the catheter in accordance with the principles of the present invention.
Figure 4:
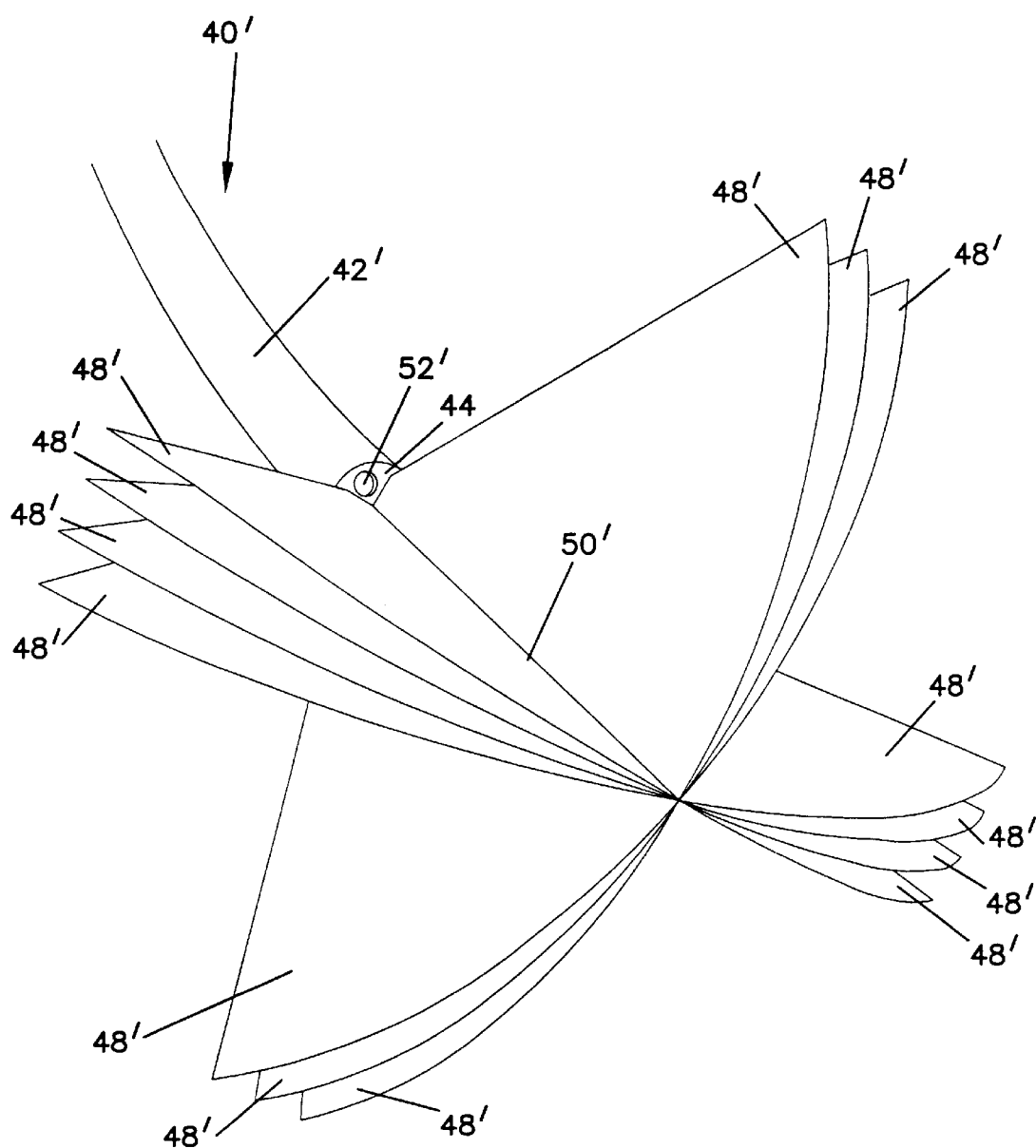
FIG. 4 is a partial schematic view of a second embodiment of a catheter system having an end-mounted multiplane transducer generating sequential imaging planes at an end of the catheter in accordance with the principles of the present invention.

Referring to FIGS. 1 and 4, a catheter system 40 (a partial view) is shown in accordance with principles of the present invention. The catheter system 40 has a catheter body 42. The catheter body 42 is shown as a generic embodiment. Detailed illustrations of the catheters are generally disclosed in U.S. Pat. Nos. 5,325,860 and 5,345,940, issued to Seward, et al., which are hereby incorporated by reference for other parts of the catheter body 42 not shown in FIGS. 1 and 4.

The catheter body 42 is an elongated flexible body which can be inserted into underfluid cavities of a body structure. The catheter body 42 has a distal end 44 and a proximal end (at the other side of the catheter body 42 which is not shown here).

A multiplane ultrasound transducer array 46 is rotatably mounted proximate the distal end 44 of the catheter body 42. The multiplane ultrasound transducer array 46 is preferably a sector phased array and is rotatable through an arc up to 360°. The multiplane ultrasound transducer array 46 transmits a plurality of sequential tomographic image planes 48 which form a 3-dimensional image of the underfluid cavities of the body structure. The multiplane ultrasound transducer array 46 has an axis 50 of rotation lying in the tomographic image planes 48. The array 46 can be rotated or manipulated through an arc up to 360° by mechanical or electrical connections or other appropriate rotating means. The rotatable array 46 obtains sequential tomographic images throughout the arc of rotation, and the series of planes 48 can be electronically coalesced into a volume suitable for the making of 3-dimensional images. Three-dimensional images enhance the appreciation of underlying anatomy. The clinical application of the present invention is broad and can be applied to any body cavities where there is an appropriate interface, such as bladder, chest cavity, bronchus, etc. It is also appreciated that other types of transducers can be used in accordance with the principles of the present invention.

In FIG. 1, the multiplane ultrasound transducer array 46 is mounted facing transversely of a longitudinal axis (not shown) of the catheter body 42. Accordingly, the axis of rotation 50 is generally perpendicular to the longitudinal axis of the catheter body 42. In FIG. 4, an alternative embodiment of the catheter system 40' is shown. The multiplane ultrasound transducer array 46' is mounted facing along the longitudinal axis of the catheter body 42'. An axis of rotation 50' extends generally along the longitudinal axis of the catheter body 42'. Accordingly, the axis of rotation 50, 50' lies in the tomographic image planes 48, 48', respectively. The series of planes 48, 48' are coalesced into a volume suitable for making 3-dimensional images.

Figure 2:
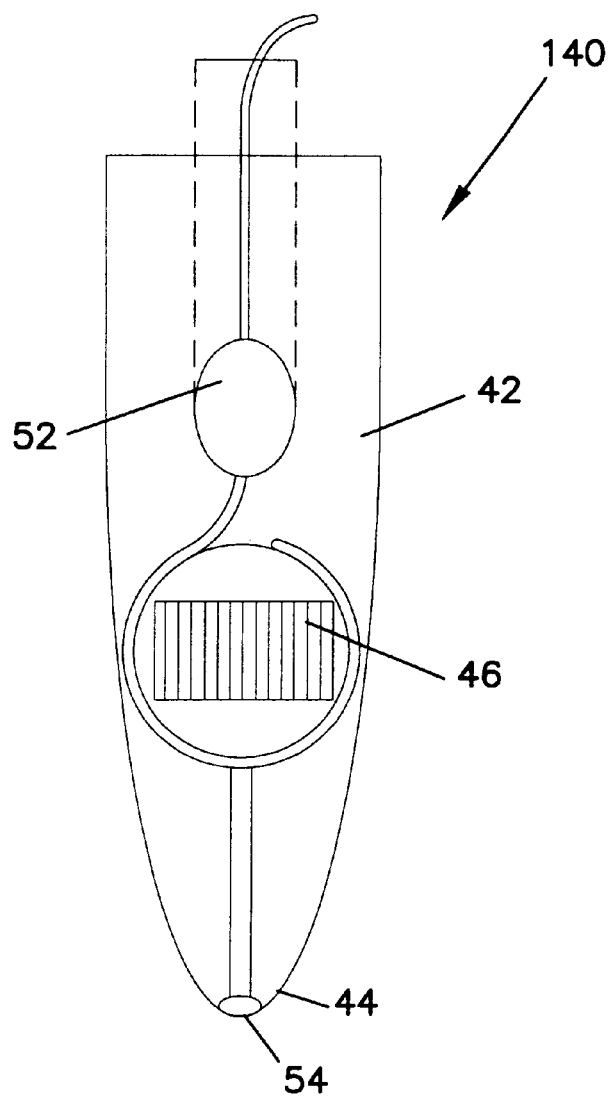
FIG. 2 is a top plane view of FIG. 1.
Figure 6:
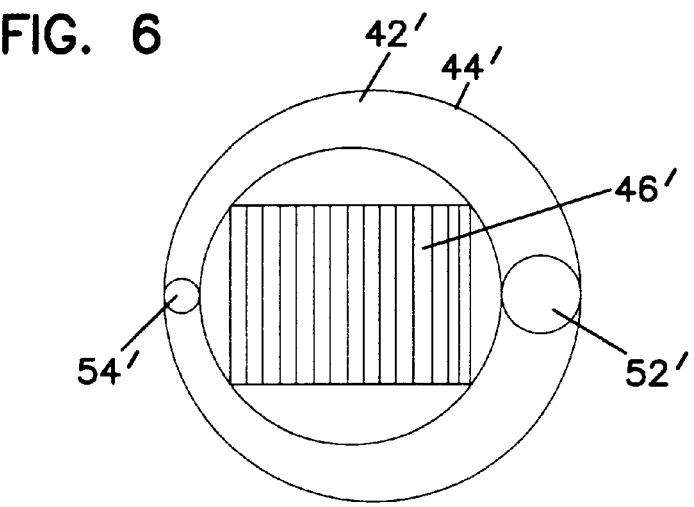
FIG. 6 is an end elevational view of FIG. 4.

The multiplane ultrasound transducer array 46, 46' are preferably a phased array (or called sector phased array). The generic configuration of the multiplane ultrasound transducer array 46 is shown in FIGS. 2 and 6. It is appreciated that other types of configurations can be used in accordance with the principles of the present invention. For example, one and one-half dimensional array, two-dimensional array, etc. can be suitably mounted in accordance with the principles of the present invention.

Figure 3:
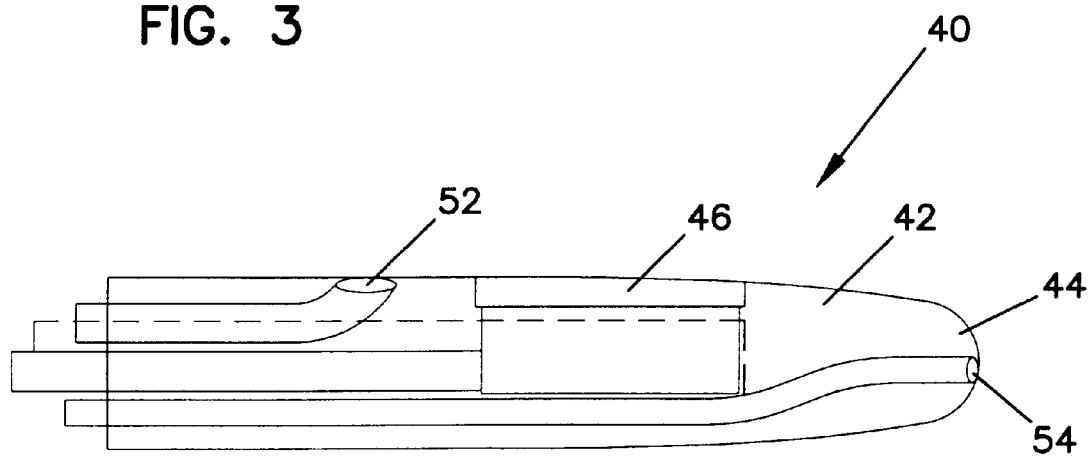
FIG. 3 is a side elevational view of FIG. 1.
Figure 7:
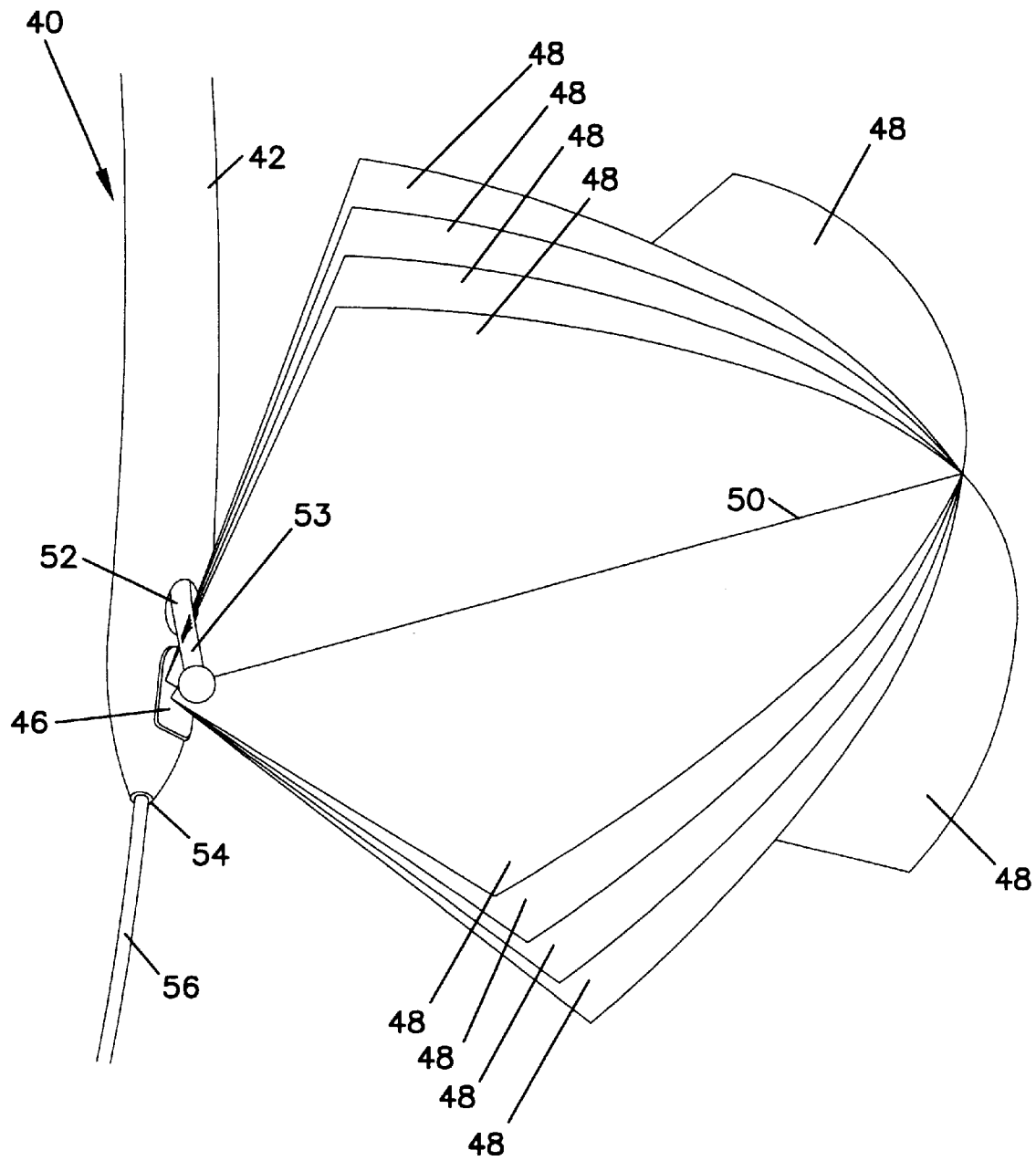
FIG. 7 is a partial schematic view of a catheter system having a medical instrument disposed in the field of view generated by a side-mounted multiplane transducer.

FIGS. 2 and 3 show top plane views and side elevational views of the side-mounted multiplane transducer as shown in FIG. 1. Further, a working port 52 is disposed in the catheter body 42 and extends from proximate the proximal end to proximate the distal end 44 of the catheter body 42. The working port 52 receives and delivers a medical instrument or other types of working tools (see later in FIGS. 7, 8) into a field of view of the multiplane ultrasound transducer. Accordingly, the operation of the medical instrument or other working tools and the reaction therefrom can be observed in a real-time fashion.

It is appreciated that in alternative embodiments, multiple working ports are disposed in the catheter for receiving and delivering multiple medical instruments or working tools into the field of view. In some other alternative embodiments, no working ports are disposed in the catheter, and medical instruments or other working tools are configured to be embedded proximate the distal end 44 of the catheter body 42 adjacent to the field of view of the transducer array 46. The embedded medical instruments or other working tools are operable in the field of view through remote manipulation.

Figure 5:
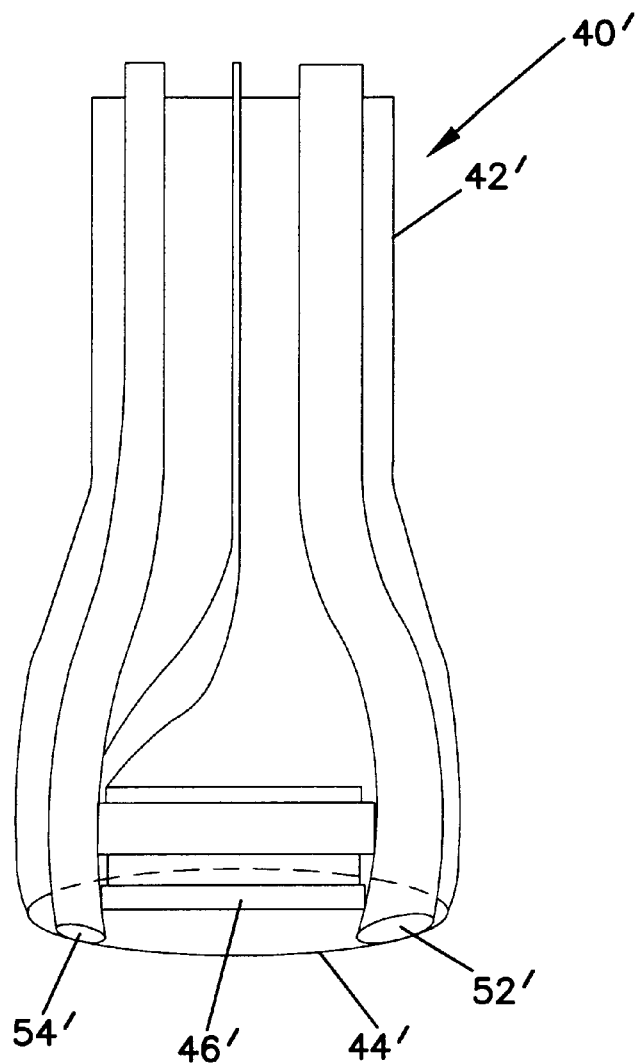
FIG. 5 is a top plane view of FIG. 4.

Similarly, FIGS. 5 and 6 illustrate the top plane view and the front end elevational view of the end-mounted multiplane ultrasound transducer array 46'. A working port 52' is disposed in the catheter body 42' and extends from proximate the proximal end to proximate the distal end 44' of the catheter body 42'. A medical instrument or other types of working tools can be delivered through the working port 52' to the distal end 44' into a field of view of the ultrasound transducer. The operation of the medical instruments or other types of working tools and the reaction therefrom can also be observed in a real-time fashion. As mentioned above, in alternative embodiments, multiple working ports are used in the catheter body 42', or no working ports are used in catheter body 42'. In the latter case, medical instruments or other working tools are operated in the field of view through remote manipulation.

Also shown in FIGS. 1–3 and 5–6 is a guidewire port 54, 54' which delivers a guidewire 56 (see FIG. 1) to proximate the distal end 44, 44' of the catheter body 42, 42'. As known in the art, the guidewire 56 is introduced into the body structure and guides the catheter into a cavity of the body structure to a desired destination. It is appreciated that the guidewire is a generic guidewire, and that other types of guiding mechanisms can be used in accordance with the principles of the present invention.

As shown in FIGS. 4–6, the axis of rotation 50' is offset from the longitudinal axis of the catheter body 42' (see clearly in FIG. 6). Off-axis imaging can be fostered in certain embodiments.

In operation of the side-mounted multiplane transducer catheter system 40 as shown in FIGS. 1–3, the catheter body 42 is guided by the guidewire 56 to proximate a desired underfluid structure. The catheter system 40 then generates the sequential tomographic image planes 48 by activating the multiplane (rotatable) phased array 46 ultrasound transducer so as to form a conical-shaped field of view. An operator can extend a medical instrument, e.g. 53,53' shown in FIGS. 7 and 8, into the field of view and operate the medical instrument 53,53' therein. The operation of the medical instrument 53,53' and the reaction therefrom are observed on a display device 58 (see FIG. 9) in a real-time fashion.

As also shown in FIG. 9, a rotation mechanism 60 is used to control the rotation of the array 46, 46'. An ultrasound control circuit 62 controls the activation and deactivation of the multiplane phased array 46 ultrasound transducer. Further, an instrument control device 64 is used to control the medical instruments and/or other working tools operated in the field of view. In addition, various diagnostic/measurement devices 66 receive the signals from the ultrasound control circuit 62 to diagnose and measure conditions of underfluid environment. The ultrasound control circuit 62 can collect sets of tomographic images and coalesce these images into a 3-dimensional volume.

In a preferred embodiment, the catheter body 42 or 42' has a dimension of 5–15 French diameter and 40 to 120 cm length. A guidewire port 54 is approximate 0.025–0.038 inch diameter. The working port 52, 52' is approximate 4-10 French diameter. It is appreciated that other dimensions of these ports of the catheter body 42, 42' can be used in accordance with the principles of the present invention. Many clinical applications can use the present invention for enhanced visualization of therapeutic or diagnostic tools or procedures within a visual field of ultrasound. For example, underfluid surgery and/or diagnostics can be better obtained with the use of the present invention of a unique application of a multiplane (rotatable) transducer to an underfluid catheter system.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An underfluid diagnostic and/or therapeutic catheter apparatus, comprising:

a catheter body having a proximal end and a distal end defining a longitudinal axis, said catheter body having a dimension insertable into a blood-type vessel; and a multiplane phased array ultrasound transducer rotatably mounted proximate the distal end of said catheter body for rotation about an axis;

whereby said multiplane phased array ultrasound transducer generates a plurality of sequential tomographic image planes to form a three-dimensional image of an underfluid structure with the axis of rotation lying in the tomographic image planes.

2. A method of diagnosing and/or imaging an underfluid structure, comprising the steps of:
  providing a catheter apparatus comprising:
    a catheter body having a proximal end and a distal end defining a longitudinal axis, the catheter body having a dimension insertable into a blood-type vessel; and
    a multiplane phased array ultrasound transducer, the multiplane phased array ultrasound transducer rotatably mounted proximate the distal end of the catheter body for rotation about an axis and capable of generating a plurality of sequential tomographic image planes to form a three-dimensional image;
  positioning the catheter proximate the underfluid structure; and
  generating a plurality of sequential tomographic images to form a three-dimensional image of the underfluid structure with the axis of rotation lying in the tomographic image planes.

3. The method of claim 2, wherein the multiplane phased array ultrasound transducer is mounted facing transversely of the longitudinal axis of the body, the axis of rotation being generally perpendicular to the longitudinal axis of the body.

4. The method of claim 2, wherein the multiplane phased array ultrasound transducer is mounted facing along the longitudinal axis of the body, the axis of rotation being generally along the longitudinal axis of the body.

5. The method of claim 2, further comprising extending a medical instrument from proximate the proximal end to proximate the distal end of the catheter body and operating on the underfluid structure within a field of view of the three-dimensional image.

6. An underfluid diagnostic and/or therapeutic intravascular catheter apparatus, comprising:
  a catheter body having a proximal end and a distal end defining a longitudinal axis, said catheter body having a dimension insertable into and a material suitable for a blood-type vessel;
  a multiplane phased array ultrasound transducer for producing a plurality of ultrasound beams, said multiplane phased array ultrasound transducer rotatably mounted proximate the distal end of said catheter body for rotation about an axis;
  whereby said multiplane phased array ultrasound transducer generates a plurality of sequential tomographic image planes to form a three-dimensional image of an underfluid structure with the axis of rotation lying in the tomographic image planes; and
  a medical instrument disposed proximate the distal end of said catheter body and operable within a field of view of the three-dimensional image.

7. The intravascular catheter apparatus in accordance with claim 6, wherein the multiplane phased array ultrasound transducer is a sector phased array.

8. The intravascular catheter apparatus in accordance with claim 7, wherein the multiplane phased array ultrasound transducer is rotatable through an arc up to 360 degrees.

9. The intravascular catheter apparatus in accordance with claim 8, wherein the multiplane phased array ultrasound transducer is mounted facing transversely of the longitudinal axis of the body, the axis of rotation being generally perpendicular to the longitudinal axis of the body.

10. The intravascular catheter apparatus in accordance with claim 8, wherein the multiplane phased array ultrasound transducer is mounted facing along the longitudinal axis of the body, the axis of rotation extending generally along the longitudinal axis of the body.

11. The intravascular catheter apparatus in accordance with claim 10, wherein the axis of rotation is offset from the longitudinal axis of the body.

12. The intravascular catheter apparatus in accordance with claim 6, wherein the catheter body has the dimension of 5–15 French diameter (1 French=⅓ millimeter).

13. The intravascular catheter apparatus in accordance with claim 12, wherein the catheter body has a length of 40–120 cm.

14. A method of diagnosing and/or imaging an underfluid structure, comprising the steps of:
  providing a catheter apparatus comprising:
    a flexible catheter body having a proximal end and a distal end defining a longitudinal axis, said catheter body having a dimension and material insertable into and suitable for a blood-type vessel;
    a multiplane phased array ultrasound transducer producing a plurality of ultrasound beams, the multiplane phased array ultrasound transducer rotatably mounted proximate the distal end of the catheter body for rotation about an axis and capable of generating a plurality of sequential tomographic image planes to form a three-dimensional image; and
    a medical instrument disposed proximate the distal end of the catheter body and operable within a field of view of the three-dimensional image;
  positioning the catheter proximate the underfluid structure;
  generating a plurality of sequential tomographic images to form a three-dimensional image of the underfluid structure with the axis of rotation lying in the tomographic image planes; and
  extending the medical instrument out of a working port of the catheter body and operating on the underfluid structure within a field of view of the three-dimensional image.

15. The method of claim 14, wherein the multiplane phased array ultrasound transducer is mounted facing transversely of the longitudinal axis of the body, the axis of rotation being generally perpendicular to the longitudinal axis of the body.

16. The method of claim 14, wherein the multiplane phased array ultrasound transducer is mounted facing along the longitudinal axis of the body, the axis of rotation being generally along the longitudinal axis of the body.

17. An underfluid diagnostic and/or therapeutic intravascular catheter apparatus, comprising:
  a flexible catheter body having a proximal end and a distal end defining a longitudinal axis, said catheter body having a dimension and material insertable into and suitable for a blood-type vessel;
  a multiplane phased array ultrasound transducer for producing a plurality of ultrasound beams, said multiplane phased array ultrasound transducer rotatably mounted proximate the distal end of said catheter body for rotation about an axis;
  whereby said multiplane phased array ultrasound transducer generates a plurality of sequential tomographic image planes to form a three-dimensional image of an underfluid structure with the axis of rotation lying in the tomographic image planes.

18. The intravascular catheter apparatus in accordance with claim 17, wherein the multiplane phased array ultrasound transducer is a sector phased array.

19. The intravascular catheter apparatus in accordance with claim 18, wherein the multiplane phased array ultrasound transducer is rotatable through an arc up to 360 degrees.

20. The intravascular catheter apparatus in accordance with claim 19, wherein the multiplane phased array ultrasound transducer is mounted facing transversely of the longitudinal axis of the body, the axis of rotation being generally perpendicular to the longitudinal axis of the body.

21. The intravascular catheter apparatus in accordance with claim 19, wherein the multiplane phased array ultrasound transducer is mounted facing along the longitudinal axis of the body, the axis of rotation extending generally along the longitudinal axis of the body.

22. The intravascular catheter apparatus in accordance with claim 21, wherein the axis of rotating is offset from the longitudinal axis of the body.

23. The intravascular catheter apparatus in accordance with claim 17, further comprising a medical instrument operable within a field of view of the three-dimensional image and a working port disposed in the catheter body extending from proximate the proximal end to proximate the distal end for receiving the medical instrument.

24. The intravascular catheter apparatus in accordance with claim 17, wherein the catheter body has the dimension of 5–15 French diameter (1 French=⅓ millimeter).

25. The intravascular catheter apparatus in accordance with claim 24, wherein the catheter body has a length of 40–120 cm.

* * * * *